United States Patent
Ortmaier et al.

(10) Patent No.: US 8,831,779 B2
(45) Date of Patent: Sep. 9, 2014

(54) MEDICAL ROBOT AND METHOD FOR MEETING THE PERFORMANCE REQUIREMENTS OF A MEDICAL ROBOT

(75) Inventors: Tobias Ortmaier, Hemmingen (DE); Marc-Walter Ueberle, Friedberg (DE)

(73) Assignee: KUKA Laboratories GmbH, Augsburg (DE)

( * ) Notice: Subject to any disclaimer, the term of this patent is extended or adjusted under 35 U.S.C. 154(b) by 891 days.

(21) Appl. No.: 12/991,196

(22) PCT Filed: May 5, 2009

(86) PCT No.: PCT/EP2009/055408
§ 371 (c)(1),
(2), (4) Date: Dec. 9, 2010

(87) PCT Pub. No.: WO2009/135835
PCT Pub. Date: Nov. 12, 2009

(65) Prior Publication Data
US 2011/0118872 A1 May 19, 2011

(30) Foreign Application Priority Data
May 8, 2008 (DE) .......................... 10 2008 001 664

(51) Int. Cl.
*G06F 19/00* (2011.01)
*A61B 19/00* (2006.01)
(52) U.S. Cl.
USPC ........... 700/254; 700/250; 700/256; 700/257; 700/261; 700/262; 318/590

(58) Field of Classification Search
USPC ......... 700/245, 247, 250, 254, 253, 256, 257, 700/261, 262; 606/1; 901/9, 14; 703/1, 6; 33/503; 318/568.18, 590
See application file for complete search history.

(56) References Cited

U.S. PATENT DOCUMENTS

| | | |
|---|---|---|
| 2004/0034282 A1 | 2/2004 | Quaid, III |
| 2005/0251156 A1 | 11/2005 | Toth et al. |
| 2007/0005002 A1 | 1/2007 | Millman et al. |
| 2007/0144298 A1 | 6/2007 | Miller |
| 2009/0024142 A1* | 1/2009 | Ruiz Morales ................ 606/130 |
| 2010/0198402 A1* | 8/2010 | Greer et al. .................... 700/247 |

FOREIGN PATENT DOCUMENTS

| | | |
|---|---|---|
| DE | 200 10 529 U1 | 10/2000 |
| DE | 10 2004 043 514 A1 | 3/2006 |
| DE | 10 2005 011 143 A1 | 9/2006 |

(Continued)

OTHER PUBLICATIONS

European Patent Office; Search Report in International Patent Application No. PCT/EP2009/055408 dated Oct. 6, 2009; 5 pages.

(Continued)

*Primary Examiner* — Ronnie Mnacho
(74) *Attorney, Agent, or Firm* — Wood, Herron & Evans, LLP

(57) ABSTRACT

The invention relates to a medical robot (R) and a method for meeting the performance requirements of a medical robot (R). The robot (R) comprises several axes (1-6) and a controller (17). A medical tool (21-24) is fixed to a fixing device (18) on the robot (R) and the working range (30) of the robot (R) is set by the controller (17) in particular with safe techniques such that the robot (R) meets the performance requirements of the medical tool (21-24).

22 Claims, 4 Drawing Sheets

(56) References Cited

FOREIGN PATENT DOCUMENTS

Figure 1:
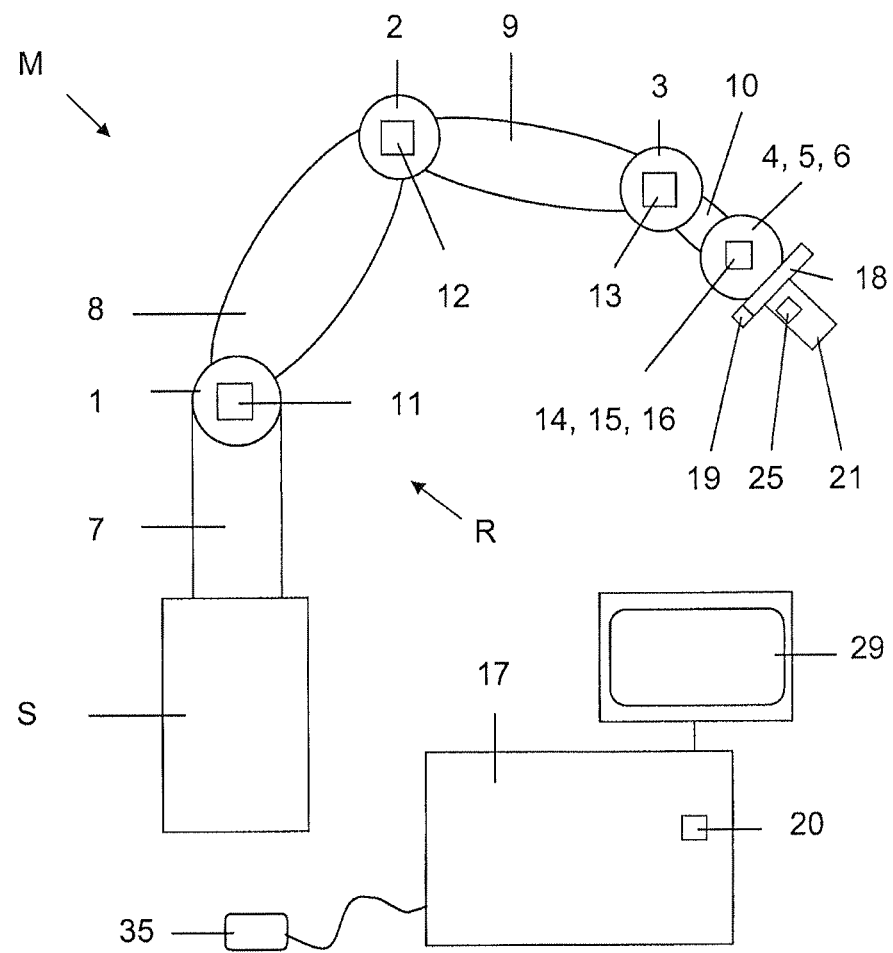

| | | |
|---|---|---|
| DE | 10 2006 061 752 A1 | 7/2008 |
| JP | 2002-36155 A | 2/2002 |
| JP | 2004-129782 A | 4/2004 |
| WO | 98/42482 A1 | 10/1998 |
| WO | 2005/110267 A1 | 11/2005 |
| WO | 2008/040426 A1 | 4/2008 |
| WO | 2008/133956 A2 | 11/2008 |

OTHER PUBLICATIONS

V. Nedeljkovic-Groha et al.; "Objektnahe Datenhaltung im Fertigungsbereich"; Carl Hanser Verlag, Munchen 1993; ZwF 88 (1993) 1; pp. 20-23.

* cited by examiner

MEDICAL ROBOT AND METHOD FOR MEETING THE PERFORMANCE REQUIREMENTS OF A MEDICAL ROBOT

The invention relates to a medical robot and a method for meeting the performance requirements of a medical robot.

Robots are working machines, which are equipped with tools for automatic handling and/or processing of objects, and are programmable in a plurality of motion axes, for example with regard to orientation, position and process sequence. Robots normally have programmable controllers (controlling devices) which control the sequences of motions of the robot during operation.

Robots may be used for example for medical and/or clinical applications. Because of a relatively broad range of applications in medical technology, there are significantly varying and in some cases even competing demands on the required operating performance of the robot used, for example in regard to working range, rigidity, payload or speed and acceleration capacity. Fulfillment of the required specification usually must be ensured for all robot configurations, in particular for the "worst case" configuration, in which the corresponding performance characteristic is at its worst. This is required for example in the mechanical overload test according to IEC 60601-1, which must be verified in conjunction with the licensing of medical technology equipment for example in Germany for the least favorable load configuration in the working range. This may result in very conservative performance specifications for a given working range of the robot.

DE 10 2004 043 514 A1 reveals a method and a device for controlling a safety-relevant function of a machine. The machine comprises a machine controller, a sensor for detecting an object, for example a person, within a monitoring zone, and an evaluation unit to determine a danger zone and to trigger the safety-relevant function when the detected object intrudes into the danger zone. To determine the danger zone, the evaluation unit is coupled with the machine controller, and the evaluation unit is designed to derive the requisite parameters for determining the danger zone from the control signals used by the machine controller to control the motion of the machine.

The object of the invention is to create prerequisite conditions, on the basis of which the performance specifications of the robot may be chosen less conservatively.

The object of the invention is fulfilled by a method for satisfying the performance requirement of a medical robot, having the following procedural steps:
  attaching of a medical tool to an attaching device of a robot having a plurality of axes and a control device, and
  adjustment of the working range of the robot by the control device, in particular using secure technology, in such a way that the robot satisfies the performance requirement of the application to be carried out using the medical tool.

The object of the invention is also fulfilled by a medical robot having a robot arm with a plurality of movable axes and having an attaching device and a control device to move the axes of the robot arm with the aid of drives, the control device being set up, in particular using secure technology, to adjust the working range of the robot in such a way that the robot satisfies a performance requirement of the application to be carried out with the medical tool.

It is thus possible to carry out the method according to the invention using the robot according to the invention.

One aspect of the method according to the invention is adjusting the working range of the robot, so that the robot satisfies the performance requirement of the application to be carried out with the medical tool. The performance requirement of the application includes for example the required speed capacity, the required acceleration capacity, the load acting on the robot, a rigidity demanded of the robot due to the use of the robot, the braking distance of the robot, and/or a manipulability of the robot.

The working range of a robot is the permissible zone in which the robot may work and travel. When the robot is in operation, in particular all of the axes of the robot must be within the working range. The maximum working range is the range within which the robot is able to move on the basis of its mechanical extension. However, as a rule the working range is only part of this maximum possible range.

The working range of a robot may be delimited or set mechanically, or else with the aid of a computer program running on the control device of the robot. According to the method according to the invention, the working range of the robot is set by the control device, for example in that the aforementioned computer program prevents the exes from being moved outside of the defined working range during operation of the robot.

The robot according to the invention is intended in particular to be provided with various medical tools; that is, during operation in particular various medical tools, such as medical instruments, are to be attached to the attaching device of the robot according to the invention. The attaching device is for example a flange of the robot. Such a scenario arises in particular in surgical use, in which the same robot is employed for various tasks and potentially is provided with various tools. So as not to have to design the robot according to the invention for the "worst case," the control device of the robot according to the invention matches the working range to the tool attached to, or to be attached to, the attaching device, so that the robot satisfies the performance requirement of the application to be carried out with the medical tool. This results for example in a dynamic adjustment of the working range of the robot, depending on the medical tool used or depending on the performance requirement of the latter.

The adjustment of the working range is accomplished for example by limiting the travel distance of the joints of the robot, the Cartesian workspace and/or the so-called zero space, depending in particular on the demanded performance requirement. Zero space designates the joint angle space of a redundant robot, in which it is possible to reconfigure the robot joints in such a way that the situation (position and orientation) of the end effector of the robot in space remains unchanged.

The adjustment of the working range may be done in particular using secure technology.

A relatively high mechanical rigidity of the robot may be necessary for example for drilling applications in orthopedics, in which comparatively high interactive forces may occur, to achieve high operational precision. Hence the robot according to the invention may be set up in such a way that its control device limits the working range to regions of relatively high rigidity when using a tool intended for the drilling application, whereby the performance criterion in effect for this application is increased.

In addition to the force or torque capacity of the actuators of the robot, the overload test per IEC 60601-1, which is required for licensing for example in Germany, represents a limit for the payload capacity of the robot. To comply with the overload test, the robot must be able to hold a multiple of the specified payload and of the dead weight for a defined time period, in particular with activated brakes and/or under automatic control. This must be ensured for all planned robot configurations, including in particular for the "worst case."

The adjustment of the working range of the robot depending on the medical tool used may result in an increase in the permissible payload of the robot.

Applications having requirements for the speed to be reached by the medical tool attached to the robot may require exclusion of robot configurations in close proximity to kinematic singularities. A corresponding limitation of the working range may be used in this case to satisfy the required specification. Requirements for the speed performance occur for example in applications in which the robot is to compensate for the movement of body parts (e.g., breathing motion).

Compliance with the required acceleration capacity may possibly not be guaranteed over the entire working range, and therefore may be attainable only by limiting the working range. Possible applications in turn involve the use of motion compensation. In addition, applications having high safety requirements may necessitate limiting the braking distance. This can be achieved by limiting the working range to regions with sufficiently high brake acceleration. Low maximum acceleration of the robot is also conceivable; in the event of an error, this results in the robot being able to build up little kinetic energy before the brakes take effect, and also traveling only a short distance.

According to one variant of the method or robot according to the invention, the robot automatically obtains information about the tool attached to the robot, in order to determine the working range that satisfies the performance requirement. This can be accomplished for example by having the tool include a data medium, in which data are stored that contain information about the tool and/or about the performance requirement of the application to be carried out with the medical tool. The data medium may be read out for example using an appropriate reading device which is situated for example on the robot, which enables the robot according to the invention to adjust the control device automatically, on the basis of the data read out, in such a way that it matches the working range of the robot to the attached tool. However, it may also be provided that the readout of the data must be initiated manually, and/or that the adjustment of the working range must be confirmed manually. The information necessary for the performance requirement is for example a load parameter of the attached tool. The nature of the treatment may also play a role in determining the performance requirements.

The readout of the data from the data medium and/or the transmission of the read data from the data medium to the control device may be done for example using secure technology. The data are also stored in particular using secure technology. Secure data transmission may be achieved for example through the use of a checksum. It is also possible for data to be written back to the data medium using secure technology.

The data medium may be a contact-based or a non-contact data medium. In particular, the data medium may be a transponder. A transponder in this case is a device which, on the basis of a signal received wirelessly, coming from a reading device, automatically generates another signal and sends it wirelessly to the reading device. Transponders make use of so-called RFID (radio frequency identification) technology, and are also known as RFID tags. Transponders may be active and passive transponders. Active transponders have an active energy source of their own, such as a battery or a rechargeable battery. Passive transponders, in contrast, do not include an active energy source, and are supplied with electrical energy by the electromagnetic field of the reading device, for example by a capacitor of the transponder being charged by the electromagnetic field of the reading device.

According to another embodiment of the method or robot according to the invention, information about the tool is input into the control device, for example with the aid of input means of the robot, so that the working range may be matched to the medical tool that is attached or is to be attached on the basis of the information entered.

Since the robot according to the invention is used in the medical or surgical environment, it is possible for example that only a medical instrument is used as the tool to be attached to the robot for a particular medical treatment or for a particular surgical procedure. The instrument may be selected for example before the procedure or before the treatment. The performance requirements may then be conveyed by the application software to the control device, in particular using secure technology, for example secured by a checksum. The working range of the robot is limited on the basis of this information, in particular likewise using secure technology. The limitation may take place for example by way of a calculation specification or a previously obtained table. Velocities, torques, accelerations, etc., may also be limited.

If more than one instrument is used in the instrument or treatment, and/or if the performance requirement change with the work step, the procedure just described may be repeated.

But if an unknown instrument is used, the robot can undertake an automatic load determination, for example by moving the instrument into various suitably chosen identification poses and reading out the corresponding joint torque values. Both moving to the poses and reading out the torques preferably occur in this case using secure technology. From this information it is now possible, preferably also using secure technology, to calculate the load parameters of the instrument and to limit the performance requirements, in particular the working range.

Accordingly it is provided, according to one variant of the method or robot according to the invention, to ascertain at least one load parameter of the tool attached to the robot by the robot, in particular using secure technology, in order to ascertain the performance requirement for the tool. This may be achieved by moving the tool with the aid of the robot to various positions, in particular using secure technology, and ascertaining torques acting on the axes of the robot or torques produced by drives of the robot, in particular using secure technology. It is also possible, however, to move the tool to various positions with the aid of the robot, in particular using secure technology, and to ascertain forces and/or torques acting on the attaching device of the robot, in particular using secure technology. The load parameter is in particular the mass of the tool and/or its center of gravity.

Figure 2:
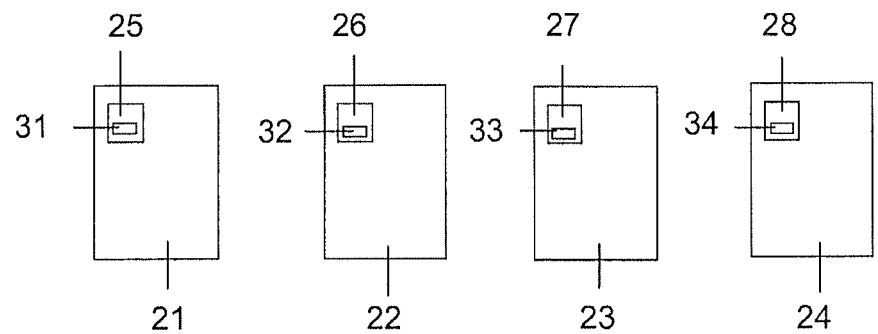
Figure 3:
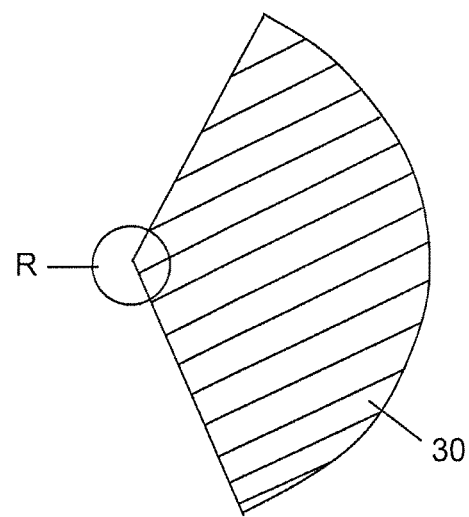
Figure 4:
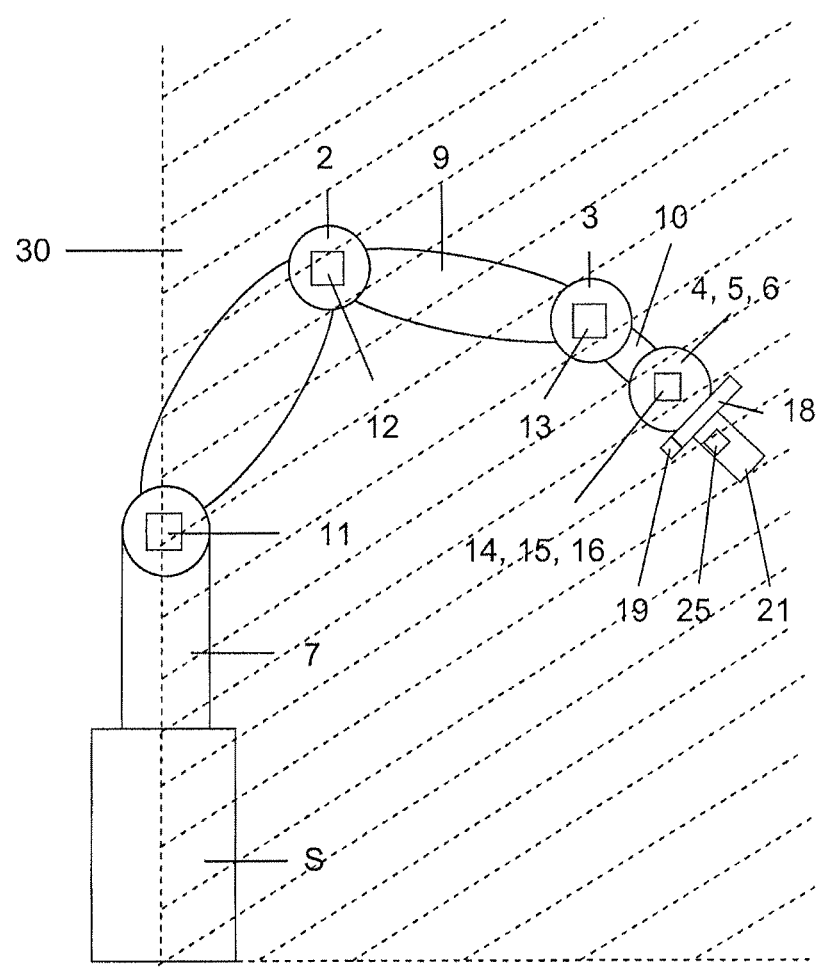

Examples of exemplary embodiments of the invention are depicted in the accompanying schematic drawing. The figures show the following:

FIG. 1 a robot,

FIG. 2 a plurality of tools that are attachable to the robot,

FIG. 3 a top view of the robot with a working range of the robot,

FIG. 4 a side view of the robot with its working range, and

Figure 5:
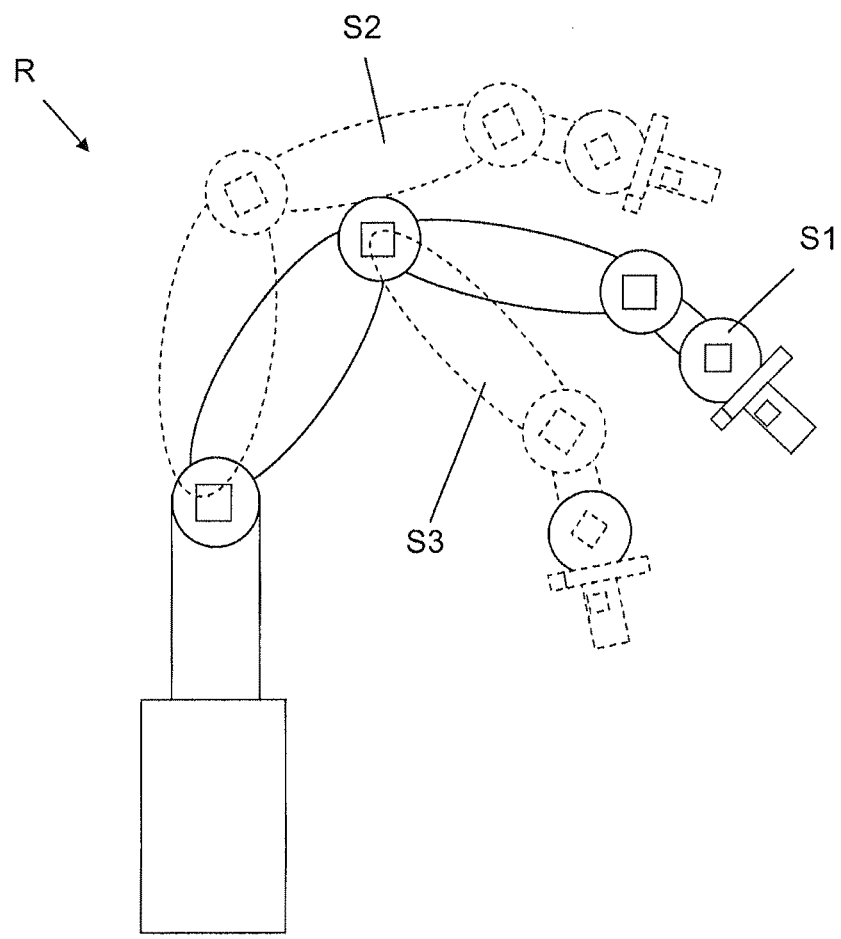

FIG. 5 a plurality of axis positions of the robot.

FIG. 1 shows a robot R having a robot arm M, which in the case of the present exemplary embodiment is attached to a base S. Robot arm M represents essentially the movable part of the robot, and includes a plurality of axes 1-6, a plurality of levers 7-10 and a flange 18, to which to which medical tools 21-24 shown in FIG. 2 may be attached. Tools 21-24 may be medical instruments, in particular surgical instruments, as provided in the case of the present exemplary embodiment.

Each of the axes 1-6 is moved with a drive, for example an electric drive 11-16, which are electrically connected in a non-depicted manner to a control computer 17 of robot R, so that control computer 17 or a computer program running on control computer 17 is able to activate electric drives 11-16 in such a way that the position of flange 18 of the robot can be oriented essentially freely in space. Electric drives 11-16 of robot R each include for example an electric motor and possibly power electronics that activate the motors.

In the case of the present exemplary embodiment, control computer 17 is designed in such a way that it, or a computer program running on it, is able to limit the working range of robot R. A working range of robot R is understood to mean the permissible zone for robot R for working and traveling. When robot R is in operation, in particular all of the axes 1-6 of robot R must be within the working range. FIGS. 3 and 4 show an example of a working range 30 of robot R set by control computer 17, preferably using secure technology, where FIG. 3 shows a top view of robot R with working range 30 and FIG. 4 shows a side view of robot R with working range 30.

In the case of the present exemplary embodiment, it is provided that control computer 17 [matches] the working range 30 of robot R dynamically to the tool 21-24 presently attached to flange 18 or satisfies the performance requirement of the application to be carried out with the tool 21-24 presently attached to flange 18.

In order that in the case of the present exemplary embodiment control computer 17 receives notification of which of tools 21-24 is presently attached to its flange 19, there is at least one RFID transponder 25-28 situated on each of the tools 21-24, which in the case of the present exemplary embodiment are passive transponders. Transponders are familiar in principle to a person skilled in the art, for which reason transponders 25-28 are not depicted in greater detail and their functionality is not explained in further detail.

In the case of the present exemplary embodiment, in each of the transponders 25-28 data 31-34 are stored which contain information about the corresponding tool 21-24. This information includes for example the mass and the center of gravity of the relevant tool 21-24. But the information may also contain a specification of the use of the tool 21-24 or of the performance requirement of the corresponding medical application, such as the permitted velocity profile, the permitted acceleration profile, or a rigidity required of robot R due to the use of the relevant tool 21-24.

Furthermore, in the case of the present exemplary embodiment there is a reading device 19 attached to flange 18 of robot R, which is connected to control computer 17 in a manner not shown.

If one of the tools 21-24 is now attached to flange 18 of robot R, then after the attaching is completed the reading device 19 transmits a signal which is received by the transponder 25-28 of the tool 21-24 attached to flange 18. In the exemplary embodiment depicted in FIG. 1, tool 21 has been attached to flange 18, whereupon transponder 25 of tool 21 receives the signal obtained from reading device 19 and thereupon automatically generates a response signal and sends it to reading device 19. The response signal includes the data 31 of tool 21. Reading device 19 receives the response signal with the data 31 from transponder 25 and conveys the data 31 to control computer 17. The readout of the data 31 and the transmission of the data 31 from reading device 19 to control computer 17 are done using secure technology, for example using a checksum.

Control computer 17 receives the data 31 and ascertains the working range 30 assigned to tool 21 on the basis of the information about the performance requirement, the mass and/or the center of gravity of tool 21. The determination of the working range 30 is done for example by way of a calculation specification or a table obtained previously and stored in control computer 17.

The determination and setting of the working range 30 assigned to tool 21 may be done for example automatically. However, it is also possible to initiate the readout of the data 31 from transponder 25 manually, for example by a person not shown in greater detail actuating an actuating means 20 of control computer 17. Additionally or alternatively, there may be provision for confirming the change of working range 30 manually.

It is also possible for control computer 17 to write to transponder 25 via a secure feedback channel, using secure technology, so that the hours of operation for example may be stored.

Instead of storing the necessary data for setting the working range 30 in a data memory situated on the tool, there may also be provision to store information about the employed tool 21-24 in control computer 17. It is thus possible for the person at control computer 17 to make an entry about the employed tool 21-24, for example by being offered a selection of tools with the aid of a display screen 29 connected to control computer 17. The person may then select the relevant tool for example by clicking with a mouse 35 connected to control computer 17. The performance requirement and the relevant load parameters (mass and weight) of the selected tool are then conveyed by the application software to control computer 17 using secure technology, for example secured by a checksum. The working range 30 of robot R is limited on the basis of this information, likewise using secure technology. The configuration by the operator is likewise preferably done using secure technology.

If no information is known about the tool 21-24 or its performance requirement, then there is provision in the case of the present exemplary embodiment to ascertain the mass and the center of gravity of the tool 21-24 attached to robot R in the following way:

Control device 17 controls electric drives 11-16 in such a way that axes 1-6 are in predetermined positions. This is illustrated in FIG. 5 by depicting three different axis positions S1-S3. The torques produced by electric drives 11-16 for the various axis positions S1-S3 are then ascertained, for example by analyzing the electric currents of drives 11-16 or via force and/or torque sensors integrated into robot R.

It is also possible, however, that robot R moves the tool 21 attached to its flange 18 to the various positions and ascertains [them] from forces and/or torques acting on the flange 18.

Both moving to the poses (axis positions S1-S3) and ascertaining and/or calculating the torques is preferably done here using secure technology. It is now possible from this information (also using secure technology) to calculate the load parameters (mass and center of gravity) of the tool attached to robot R and to set the relevant working range 30 accordingly.

The invention claimed is:

1. A method for configuring a medical robot to meet a performance requirement of an application to be performed by the robot, the method comprising:

attaching a medical tool to an attaching device of the robot, the robot having a plurality of axis and a control device; and adjusting a working range of the robot using the control device, such that the robot will satisfy the performance requirement with the medical tool;

wherein the performance requirement of the application includes at least one of a required velocity capacity, a required acceleration capacity, a load acting on the robot, a rigidity required of the robot due to the use of the medical tool, or a braking distance of the robot.

2. The method of claim 1 further comprising:
automatically determining information about the attached medical tool; and
determining the working range of the robot based at least in part on the automatically determined information.

3. The method of claim 1 further comprising:
obtaining requirement data stored on a data medium associated with the attached medical tool, the stored requirement data including information about the attached medical tool; and
in response to obtaining the requirement data, adjusting the control device based at least in part on the stored requirement data.

4. The method of claim 3, wherein the stored requirement data includes information about the performance requirement associated with the attached medical tool.

5. The method of claim 3, wherein automatically adjusting the control device based at least in part on the stored requirement data comprises automatically adjusting the working range of the robot.

6. The method of claim 3, wherein the data medium is a transponder, and wherein obtaining the requirement data includes obtaining the requirement data utilizing a reading device configured to interact with the transponder, the reading device being attached to the robot.

7. The method of claim 6, further comprising:
transmitting the obtained requirement data from the reading device to the control device using secure data transmission technology.

8. The method of claim 3, wherein obtaining the stored requirement data is manually initiated after attaching the medical tool.

9. The method of claim 3, wherein the working range is adjusted by the control device based on the obtained stored requirement data and a manual confirmation of the adjustment.

10. The method of claim 1 further comprising, in response to attaching the medical tool, determining a load parameter associated with the medical tool.

11. The method of claim 10, wherein determining the load parameter associated with the medical tool includes:
moving the medical tool with the robot to a plurality of positions; and
determining at least one of:
torques acting on at least one axis of the robot,
torques produced by at least one drive of the robot,
forces acting on the attaching device, or
torques acting in the attaching device.

12. The method of claim 1, further comprising:
inputting information corresponding to the medical tool into the control device, wherein the working range is adjusted based at least in part on the input information.

13. The method of claim 1, wherein the method is performed using secure data communication technology.

14. The method of claim 1, wherein the performance requirement of the application includes manipulability of the robot.

15. A medical robot configured to perform an application having a performance requirement, the medical robot comprising:
a robot arm including a plurality of moveable axes and an attaching device, the attaching device removably attaching a medical tool thereto;
a plurality of drives associated with the plurality of moveable axes and operating the respective plurality of axes to articulate the robot arm; and
a control device operatively coupled with the plurality of drives, the control device controlling operation of the plurality of drives to articulate the robot arm and adjusting a working range of the robot such that the robot will satisfy the performance requirement;
wherein the performance requirement of the application includes at least one of a required velocity capacity, a required acceleration capacity, a load acting on the robot, a rigidity required of the robot due to the use of the medical tool, or a braking distance of the robot.

16. The medical robot of claim 15, wherein the control device:
automatically determines information about the medical tool in response to the medical tool being attached to the robot; and
determines the working range of the robot based at least in part on the automatically determined information.

17. The medical robot of claim 16, wherein the medical tool includes an attached data storage device, and requirement data including information about the medical tool is stored on the data storage device, the robot further comprising:
a reading device in communication with the control device, the reading device interacting with the data storage device in response to the attachment of the medical tool and obtaining the requirement data stored thereon;
wherein the control device adjusts the working range based at least in part on the requirement data.

18. The medical robot of claim 17, wherein the data storage device is a transponder.

19. The medical robot of claim 15, wherein the control device further determines a load parameter associated with the medical tool in response to the attachment of the medical tool, and determines the performance requirement based at least in part on the load parameter.

20. The medical robot of claim 19, wherein the control device determines the load parameter by moving the medical tool with the robot to a plurality of positions; and determining at least one of:
torques acting on at least one axis of the robot,
torques produced by at least one drive of the robot,
forces acting on the attaching device, or
torques acting in the attaching device.

21. The medical robot of claim 15, further comprising:
an input device associated with the control device;
the control receiving information associated with the medical tool input by a user via the input device, and in response to receiving the information, adjusts the working range of the robot based at least in part on the received information.

22. The medical robot of claim 15, wherein the performance requirement of the application includes manipulability of the robot.

* * * * *

UNITED STATES PATENT AND TRADEMARK OFFICE
CERTIFICATE OF CORRECTION

| | | |
|---|---|---|
| PATENT NO. | : 8,831,779 B2 | Page 1 of 1 |
| APPLICATION NO. | : 12/991196 | |
| DATED | : September 9, 2014 | |
| INVENTOR(S) | : Tobias Ortmaier et al. | |

It is certified that error appears in the above-identified patent and that said Letters Patent is hereby corrected as shown below:

In the Specification:

Column 2,
Line 19 reads "prevents the exes from" and should read -- prevents the axes from --.

Column 4,
Lines 21-22 read "If more than one instrument is used in the instrument or treatment, and/or if the performance requirement change with" and should read -- If more than one instrument is used in the procedure or treatment, and/or if the performance requirements change with --.

Column 4,
Line 50 reads "accompanying drawing" and should read -- accompanying drawings --.

Column 4,
Line 62 reads "flange 18, to which to which medical tools" and should read -- flange 18, to which medical tools --.

In the Claims:

Claim 1, Column 6,
Line 59 reads "the robot having a plurality of axis and" and should read -- the robot having a plurality of axes and --.

Signed and Sealed this
Ninth Day of June, 2015

Michelle K. Lee
*Director of the United States Patent and Trademark Office*